United States Patent
Gubernick et al.

(10) Patent No.: US 6,860,874 B2
(45) Date of Patent: Mar. 1, 2005

(54) TAMPON, PARTICULARLY FOR FEMININE HYGIENE

(75) Inventors: David Gubernick, Cherry Hill, NJ (US); William G. F. Kelly, Middlesex, NJ (US); Hans Werner Schoelling, Ennepetal (DE)

(73) Assignee: Johnson & Johnson GmbH (DE)

( * ) Notice: Subject to any disclaimer, the term of this patent is extended or adjusted under 35 U.S.C. 154(b) by 0 days.

(21) Appl. No.: 10/317,381

(22) Filed: Dec. 12, 2002

(65) Prior Publication Data

US 2004/0030316 A1 Feb. 12, 2004

Related U.S. Application Data

(63) Continuation of application No. 09/783,844, filed on Feb. 15, 2001, now abandoned.

(51) Int. Cl.[7] .............................................. A61F 13/20
(52) U.S. Cl. .................. 604/385.18; 604/904
(58) Field of Search ........................ 604/385.18, 904, 604/11–18

(56) References Cited

U.S. PATENT DOCUMENTS

| | | | | |
|---|---|---|---|---|
| 6,183,436 B1 | * | 2/2001 | Korteweg et al. | ....... 604/96.01 |
| 6,465,713 B1 | * | 10/2002 | Gell et al. | .................. 604/383 |
| 6,570,055 B2 | * | 5/2003 | Yang et al. | .................. 604/367 |

* cited by examiner

*Primary Examiner*—John J. Calvert
*Assistant Examiner*—C. Lynne Anderson

(57) ABSTRACT

A tampon, particularly for feminine hygiene, includes an absorbent body and a variably perforated or apertured cover. The absorbent body has an introduction end, a withdrawal end, and a longitudinal main portion therebetween. The cover includes a fluid-impervious plastic material in the form of a resilient three-dimensional web having a multiplicity of perforations. The perforations are varied over the length of the tampon so that a differentiated expansion of the tampon while absorbing fluid is achievable. Preferably, the degree of perforations of the cover increases towards the withdrawal end of the tampon at least over a portion of its length.

15 Claims, 5 Drawing Sheets

TAMPON, PARTICULARLY FOR FEMININE HYGIENE

This application is a continuation of application Ser. No. 09/783,844, filed Feb. 15, 2001, now abandoned.

FIELD OF THE INVENTION

The present invention relates to a tampon, particularly for feminine hygiene, comprising a longitudinal absorbent body made of fluid absorbing fiber material and having an introduction end and a withdrawal end, a cover substantially surrounding the absorbent body and provided with fluid-pervious perforations, said absorbent body surrounded by the cover is substantially transversely pressed to its longitudinal axis into its final shape and is provided with a withdrawal cord at its withdrawal end.

BACKGROUND OF THE INVENTION

Friese et al., U.S. Pat. No. 4,816,100, discloses a fibrous tampon substantially surrounded by a nonwoven cover material. This tampon expands substantially uniformly over its total length when engaged by fluid. If the fluid is not uniformly or only partially applied to the tampon, increased fluid concentrations are developed in certain regions of the tampon which expand more quickly at these regions in comparison to other regions of the tampon. This leads to a substantially uncontrolled expansion of the tampon, depending only on the fluid concentration on and the fluid distribution to the tampon.

Therefor, what is needed is a tampon having controllable absorbency and expandability is controllable based upon its structure without additional preparation expenses and costs.

SUMMARY OF THE INVENTION

It is an object of the present invention to improve a tampon such that its absorbency and expandability is controllable without additional preparation expenses and costs caused thereby.

Therefore, I have invented a tampon, particularly for feminine hygiene, including an absorbent body and a variably perforated or apertured cover. The absorbent body has an introduction end, a withdrawal end, and a longitudinal main portion therebetween. The cover includes a fluid-impervious plastic material in the form of a resilient three-dimensional web having a multiplicity of perforations. The perforations are varied over the length of the tampon so that a differentiated expansion of the tampon while absorbing fluid is achievable. Preferably, the degree of perforations of the cover increases towards the withdrawal end of the tampon at least over a portion of its length.

DETAILED DESCRIPTION OF THE PREFERRED EMBODIMENTS

Figure 1:
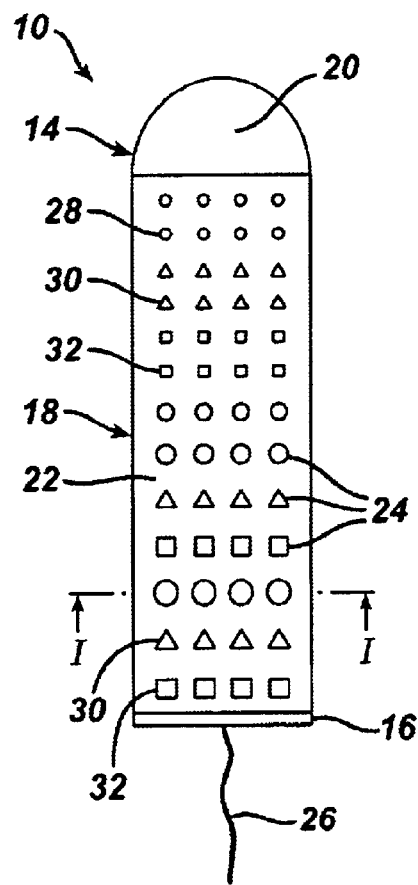
FIG. 1 shows a first embodiment of a tampon.

FIGS. 1 to 5 show a tampon 10, particularly for feminine hygiene, comprising an absorbent body 12 made of fluid absorbing fiber material and having an introduction end 14 and a withdrawal end 16 and a longitudinal main portion 18 therebetween. The tampon 10 has a constriction 20 at an end thereof. The tampon 10 is substantially enclosed within a cover 22 comprising fluid impervious plastic material in the form of a resilient three-dimensional web having a multiplicity of perforations 24. Preferably, said perforations 24 of the cover 22 are different over the length of the tampon 10, so that the tampon 10 will differently expand when applied by body fluid. A withdrawal cord 26 is attached to said tampon 10 and extends from the withdrawal end 16.

Furthermore, it can be taken from FIG. 1 that the perforation 24 are extended over the total cover 22. The perforations 24 begin directly next to the introduction end 14 of the tampon 10 and have non-uniform and various dimensions with small diameters of the perforations and/or holes 28, 30, 32 in the area of the introduction end 14 and with an alternative and increasingly enlarged structure in the area of the withdrawal end 16 of the tampon 10. This provides for an optimal diversification of the absorption velocity and the absorption capacity over the length of the tampon 10.

According to FIG. 1, the perforations 24 may consist of holes 28 having a round cross-section, holes 30 having a triangular cross-section and holes 32 having a rectangular cross-section.

The size of the opening of these holes 28, 30, 32 uniformly increases from those holes 28 adjacent to the introduction end 14 of the tampon 10 over the total length of the tampon 10 towards the withdrawal end 16. This is achieved by a greater size of said holes 28, 30, 32 in the direction of the withdrawal end 16 of the tampon 10 and also by a slight reduction of the average distance of the holes 28, 30, 32 from each other in the same direction. Thus, by choosing the geometrical configuration of the perforations 24, it is possible to vary the size of the openings of the perforations 24, whilst the observer would not notice whether the holes are in fact larger or smaller.

Preferably, the size of each of said holes 28, 30, 32 of the perforated cover 22 is increased in the direction of the withdrawal end 16 of tampon 10. As can be seen from FIGS. 1, 3, 4 and 5, such a different size of each of the holes 30 is, for example, realized by a triangle of which each of their bases is oriented towards the withdrawal end 16 of the tampon 10, so that fluid applied to the tampon 10 will be led into the direction of the withdrawal end 16 of the tampon 10, since the size of the opening of each of said holes 30 is of a greater width in the longitudinal direction of the tampon 10 than in the circumferential direction of the tampon 10. Furthermore, due to this arrangement of the holes 28, 30, 32 the absorbency of the absorbent body 12 is enhanced in the longitudinal direction of the tampon 10 towards its withdrawal end 16.

Thus, by choosing different geometrical configurations of the perforations 24, it is especially possible to vary the size of the openings of the perforations.

Figure 2:
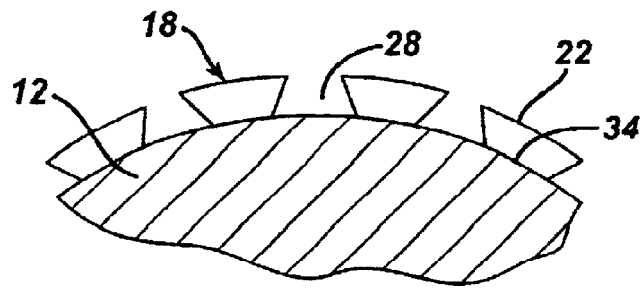
FIG. 2 shows a cross-section of a portion of a cover of said tampon according to line I—I in FIG. 1.

FIG. 2 shows a preferable cross-section of each of said holes 28 having a circular opening transversely taken to the longitudinal axis of the tampon 10. It can be seen that each of said holes 28 has a conical shape being radially inwardly extended to the outer surface 34 of the absorbent body 12. Hereby, the absorption velocity can be increased due to the fact that the effective absorbing surface area of the outer surface 34 of the absorbent body 12 is increased. However, the configuration of the holes can vary, as desired by the practitioner. For example, the holes may have substantially parallel sidewalls, or the sidewalls may be tapered from a relatively large opening at the cover surface 22 to a smaller opening at the outer surface 34 of the absorbent body 12.

Figure 3:
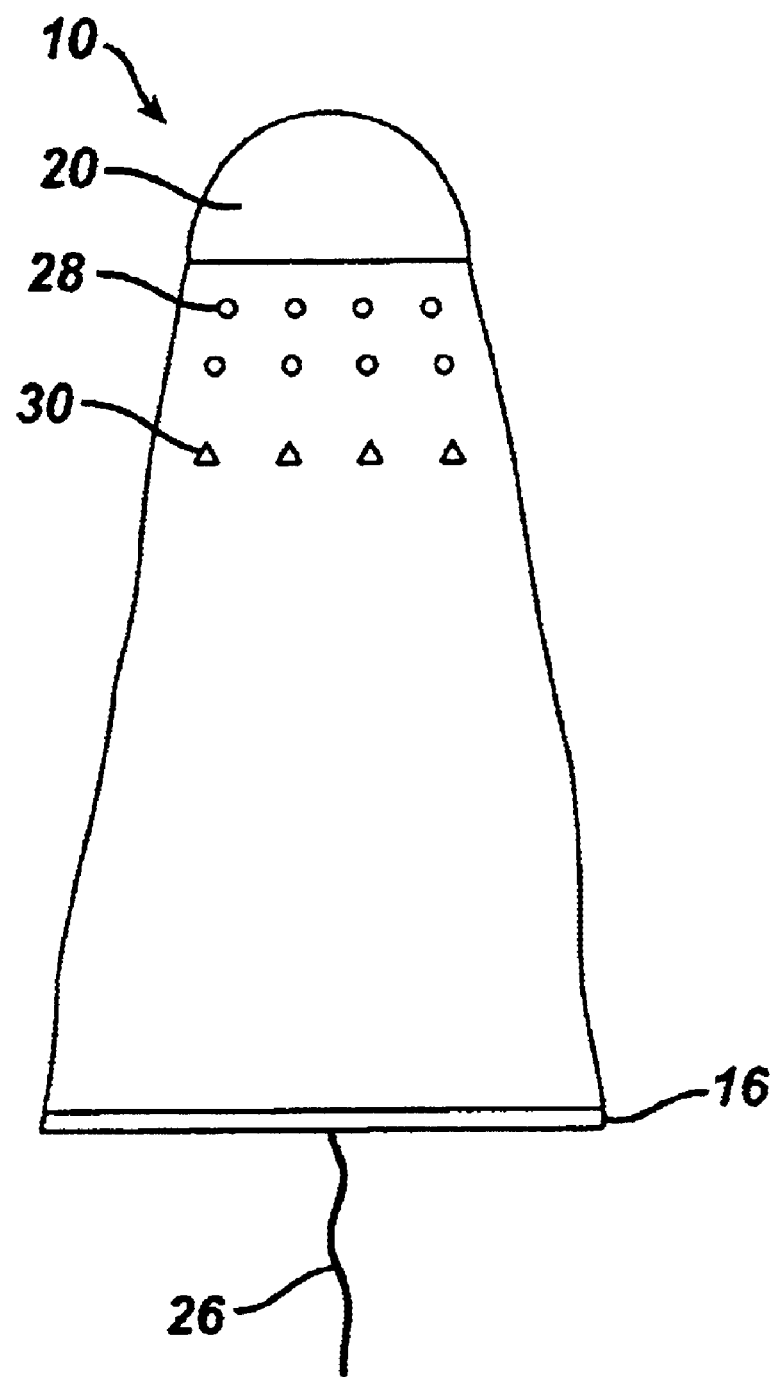
FIG. 3 shows the tampon of FIG. 1 in an expanded condition.

The tampon of FIGS. 1 and 2 is shown in FIG. 3 in an expanded condition. Due to the absorption characteristics controlled by the choice of the size and the position of the holes 28, 30, 32, the tampon 10 shows a greater expansion towards its withdrawal end 16 in comparison to the introduction end 14, so that the diameter of the expanded tampon 10 increases in the direction of its withdrawal end 16. Thus, the expanded tampon 10 has a substantially conical shape.

Figure 4:
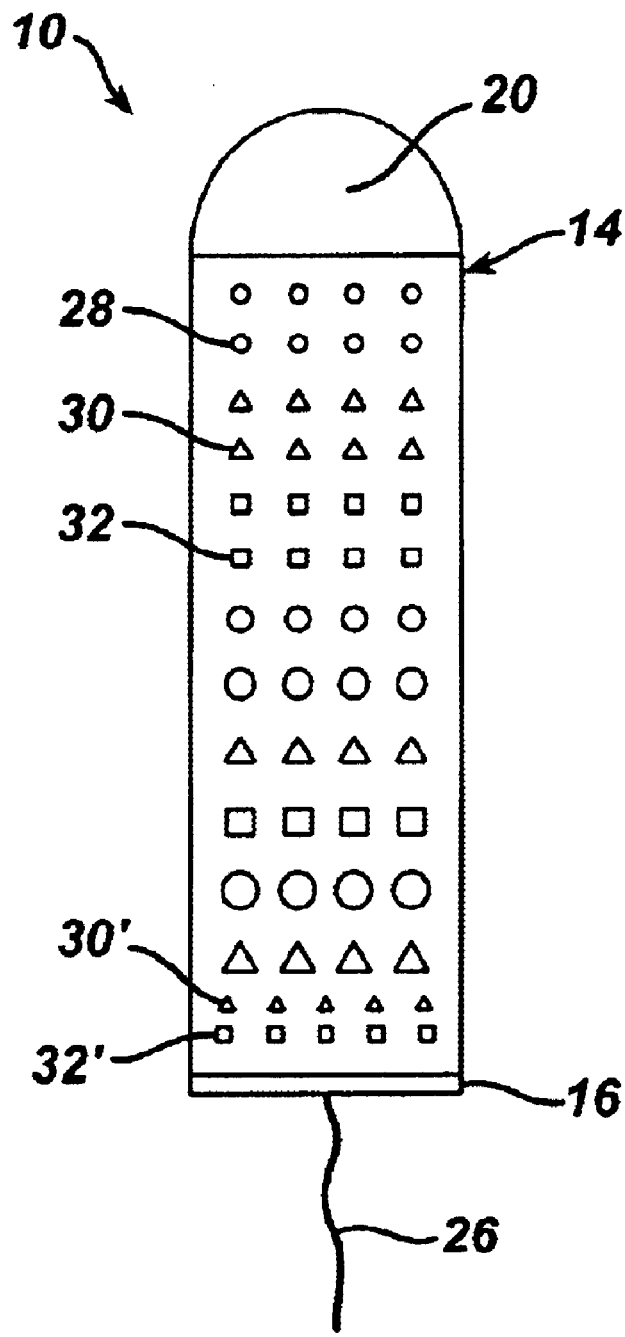
FIG. 4 shows a second embodiment of a tampon.
Figure 5:
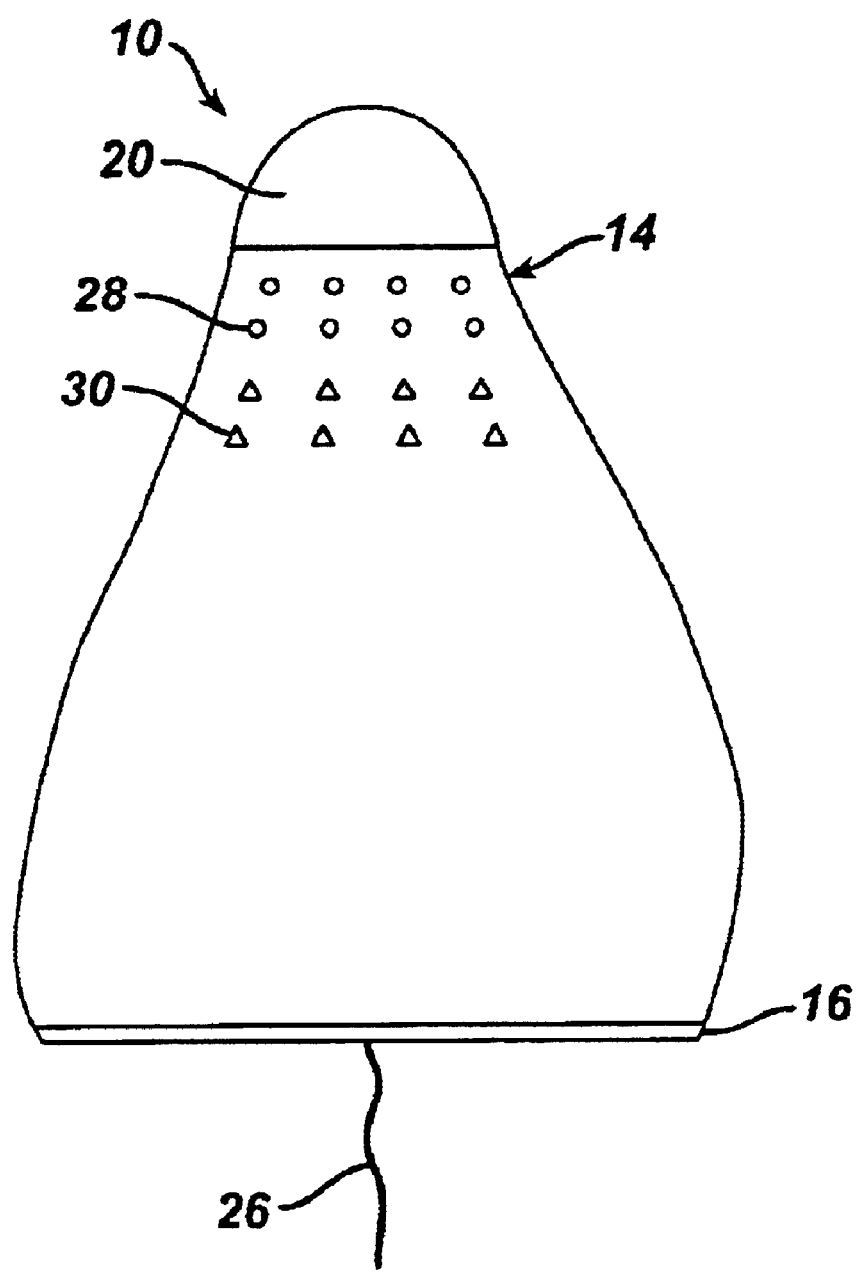
FIG. 5 the tampon of FIG. 4 in an expanded condition.

A preferable, somewhat modified embodiment of the tampon 10 is shown in FIGS. 4 and 5. The size of the perforations 30', 32' being positioned adjacent the withdrawal end 16 of the tampon 10 is much smaller than the size of those perforations 24 positioned more remotely from the withdrawal end 16 having the greatest size of all holes 28, 30, 32 of the tampon cover 22, but decrease in size towards the introduction end 14 of the tampon 10. Due to this smaller dimension of the perforations 30', 32' near the withdrawal end 16 of the tampon 10, the expansion of the withdrawal end 16 is restricted so that, when the tampon 10 is withdrawn from the body cavity, the diameter of said withdrawal end 16 of the tampon 10 is somewhat reduced as shown in FIG. 5. Thus, the tampon 10, in its expanded condition, can have a pear-shaped configuration at the time of its withdrawal. Hereby, the withdrawal of the tampon 10 is substantially facilitated for the user and without any setback of the sealing characteristics of the tampon 10. The degree of perforation 24 can affect the absorbency, particularly the absorption rate or absorption rate of the tampon, but the expansion of a special area of tampon 10, taken absolutely and in relation to each other, can be defined and adjusted.

Without any modification of the absorbent body 20 of the tampon itself, for example, by choosing different materials for partial areas of the absorbent body 20 leading to additional manufacturing costs, the absorbency of the tampon 10 can be controlled to a large extent. Since different absorbent characteristics and a different absorption capacity in dependence on the number and/or size of the perforations of the tampon cover 22 lead to a different shape of the tampon 10 when expanded, it is possible to control also these characteristics of the tampon 10 by a selected choice of the absorption characteristics. Therefore, the tampon 10 can be configured in such a manner that the sealing characteristics of the tampon 10 can be improved by the shape taken by the expanded tampon 10. Furthermore, the structure of the tampon 10 influencing the shape of the tampon 10 when expanded, can be chosen in such a manner that the introduction and the withdrawal of the tampon 10 into and out from the body cavity can be facilitated.

The cover 22 is preferably made of a plastic film of which the perforations 24 are fluid impervious, so that the number and/or the size of the perforations defines the absorption velocity or rate.

Preferably, the degree of perforation 24 or percent of the open area, of the cover 10 increases in the direction of the withdrawal end 16 of the tampon 10 over at least a portion of its length. Thereby the fluid is selectively led into the direction of the withdrawal end 16 of the tampon 10. The tampon 10 expands from the withdrawal end 16 towards the introduction end 14 having a constriction 20 with a dome or a bullet-shaped configuration. The sealing characteristics of the tampon 10 in the body cavity are noticeably increased by the enhanced expansion in the area of the withdrawal end 16 of the tampon 10 being oriented to the opening of the body cavity.

The percent of open area as defined by the degree of the perforation 24 in a particular region of the tampon can be modified in a different manner. It is possible to modify the number and/or the distance of the perforations 24 or to modify the size of the openings of the perforations. It is understandable and may be preferable to combine both of the aforementioned modifications.

Figure 6:
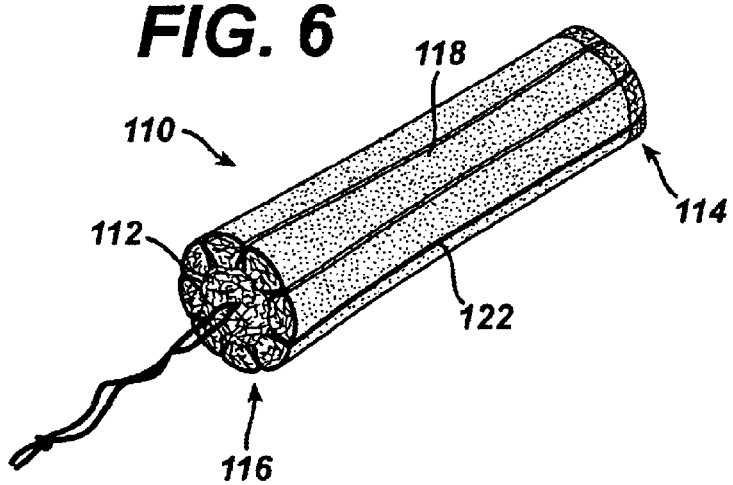
FIG. 6 shows a perspective view of a compressed tampon having a coated cover.
Figure 7:
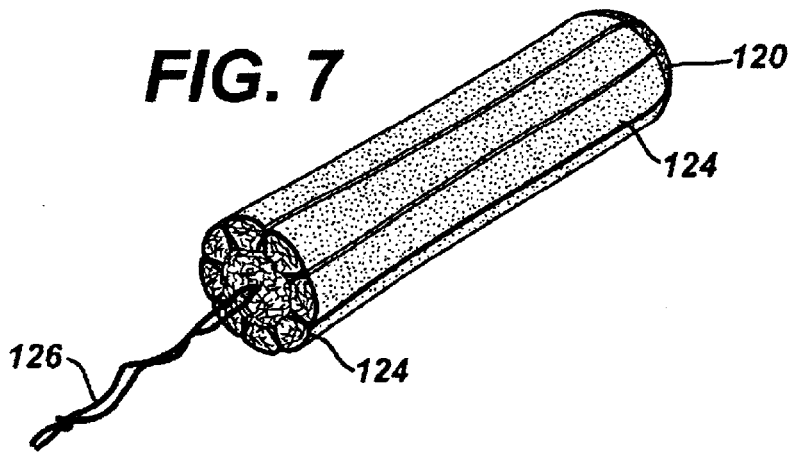
FIG. 7 shows a perspective view of a compressed tampon having a coated cover substantially extending into a dome-shaped introduction end.
Figure 8:
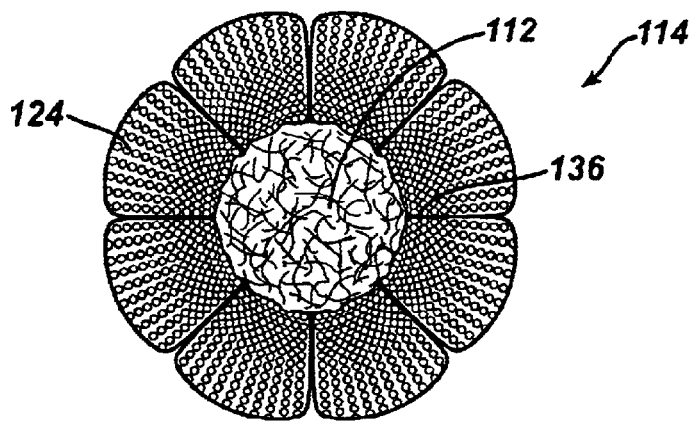
FIG. 8 shows an enlarged plan view of the introduction end of the tampon of FIG. 7.

FIGS. 6 to 8 show a tampon 110 comprising an absorbent body 112, having an introduction end 114 and a withdrawal end 116, and a longitudinal main portion 118 therebetween. The tampon further has a constriction 120 at an end thereof. The tampon 110 is substantially enclosed within a cover 122 comprising fluid-impervious plastic material in the form of a resilient three-dimensional web having a multiplicity of perforations 124 being arranged as disclosed above in connection with FIGS. 1 to 5 and only diagrammatically drawn up in FIGS. 6 to 8. Said web comprises a coating composition, such as a nonionic surfactant, on its outer surface, at least in a portion corresponding to the constricted portion 120 of the tampon 110. A withdrawal cord 126 is attached to the tampon 110 and extends from the withdrawal end 116.

The web of fluid-impervious plastic material of the present invention can be manufactured by standard processes known to those of ordinary skill in the art. For example, the base film that is to be apertured can be extruded, cast, blown, or it may be formed in other processes that will be recognized by those of ordinary skill in the art. The base film can then be apertured by any of the known processes. Several examples include hot air aperturing, and water jet aperturing. Examples of these process are disclosed in Curro, U.S. Pat. No. 4,695,422; Turi, U.S. Pat. No. 5,567,376; and Mullane, U.S. Pat. No. 4,741,877. The resulting apertured film can be slit to a desired width for use in manufacturing an absorbent article.

Special advantages are provided by a web of a fluid-impervious plastic material comprising a blend of at least two thermoplastic polymeric components, a continuous surface of a first thermoplastic polymeric component that exhibits a first melting point temperature and a dispersed surface of an immiscible second polymeric component that exhibits a second melting point temperature, lower than the first melting point temperature. When such a web is heated to a temperature between the first melting point temperature and the second melting point temperature, the second thermoplastic polymeric component is capable of forming an adhesive bond between said plastic material and the absorbent body and between said first and second surfaces of the web.

Accordingly, the circumferential surface of the absorbent body is completely covered and enclosed by said web preventing a loss of fibers and facilitating the introduction and withdrawal of the tampon into and out of the body cavity. In addition, the processing of the tampon is improved by the coating composition.

The web may have first and second surfaces, the first surface exhibiting said multiplicity of apertures therein, each of the fiber-like elements exhibiting a cross-section comprising a base portion in the plane of the first surface and a sidewall portion joined to each edge of the base portion, the sidewall portion extending generally in the direction of the second surface of the web, the intersecting sidewall portions being interconnected to one another intermediate the first and second surfaces of the web, the interconnected sidewall portions terminating substantially concurrently with one another in the plane of the second surface. The sidewall portions joined to each edge of the base portion and extending generally in the direction of the second surface of the web improve a mechanical interaction between said sidewall portion and the fiber material of the absorbent body, so that the cover is securely positioned at the outer surface of the absorbent body in its non-expanded condition and, particularly, also in its expanded position.

If the coating composition is a nonionic surfactant, it is preferably an ethoxylate, such as an ethoxylated fatty acid polyolester, a polyoxyethylene alkyl ether, an ether of an olefinic diol, or the like. It is to be understood that the nonionic surfactants used in the tampon and in its manufacture as described herein may be commercially available. Examples thereof are marketed under the registered trademarks "TWEEN" and "BRIJ" of ICI, Atlas Chemical Division, Wilmington, Del., USA.

Preferably, the coating composition is applied to the web at coating weights up to about 0.5 grams/meter$^2$ ("gsm"). More preferably, the coating weight is about 0.1 to about 0.4 gsm, and most preferably, it is applied at a coating weight of about 0.16 to about 0.36 gsm.

The coating composition is applied to the cover at least on a portion of the tampon that is further compressed to form a constricted portion having overlapping portions of the cover folded upon each other in a substantially unbonded manner. Preferably, the constricted portion is a dome-shaped introduction end of the tampon, and therefore, in a preferred embodiment, the coated portion of the cover of the tampon allows that overlapping portions of said cover are folded upon each other in a substantially unbonded manner on the introduction end and substantially prevents a bonding between the plastic web and the absorbent body. In addition, the coating composition can reduce the frictional forces of the tampon while introducing or removing the tampon into or out of the body cavity and during processing of the tampon. Furthermore, the tampon provided with the coating composition provides an improved fluid transfer across the cover. In this connection, a dome-shaped introduction end of the tampon is especially preferable.

In this connection, it has been realized that an ejection force coaxially directed to the longitudinal axis of the pressed tampon as to eject said tampon from the press may amount to less than about 1000 N.

The absorbent structure may be any absorbent means that is capable of absorbing and/or retaining liquids (e.g., menses and/or urine). The absorbent structure can be manufactured in a wide variety of sizes and shapes and from a wide variety of liquid-absorbing materials. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibers; synthetic materials, such as polyester fibers, polyolefin fibers, absorbent foams, absorbent sponges, superabsorbent polymers, absorbent gelling materials; formed fibers, such as capillary channel fibers and multilimbed fibers; combinations of materials, such as synthetic fibers and wood pulp including coformed fibrous structures (e.g., those materials described in is Anderson et al., U.S. Pat. No. 4,100,324); or any equivalent material or combinations of materials, or mixtures of these.

Preferably, the absorbent structure comprises fibers. Preferably, the fibers are relatively stiff. One type of fibers that is particularly useful in the practice of the present invention is multilimbed fibers, such as those disclosed in Wilks et al., U.S. Pat. No. 5,458,835, the disclosure of which is herein incorporated by reference. (the fibers for fabrics having relatively high flexural rigidity). These multilimbed fibers and other fibers having a sufficient stiffness may provide further benefits to the present invention, as they can contribute to expanding the constricted portion of the tampon due to their resiliency. This may overcome the constriction that may be a result of some minor, inconsequential bonds being formed between the cover and itself or other elements of the tampon.

As shown in FIG. 8, the cover 122 extends substantially into a constriction 120, such as a dome-shaped introduction end 114. This doming causes overlapping folds 136 and other deformations to occur in the cover 122 at the domed introduction end 114. In use, the introduction end 114 of the tampon 110 can expand completely as soon as it is engaged by body fluid. This characteristic can be enhanced by the fact that said cover 122 having overlapping folds 136 at the introduction end 114 of the tampon 110 is substantially not bonded to the absorbent structure 112, so that the absorbent body 112 with its cover 122 can freely expand if engaged by body fluid.

As to manufacture the tampon of the invention, the absorbent body can comprise a section of the longitudinal fleece web. A front end in the machine direction of a perforated plastic cover strip is secured, preferably by heat-sealing, to the rear end of the section of the fiber fleece in longitudinal direction of it. Thereafter, the section of the fiber web connected with said cover strip is rolled upon itself, and the rear end of the cover strip is sealed to the outer surface of the cover strip, so that a tampon blank is formed which is completely surrounded by said plastic film. Thereafter, the tampon blank is radially pressed to its main axis to form the final shape of the tampon being provided with a withdrawal cord.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. Tampon, particularly for feminine hygiene, comprising an absorbent body having an introduction end and a withdrawal end, and a longitudinal main portion therebetween; the tampon comprising a cover comprising a fluid-impervious plastic material in the form of a resilient three-dimensional web having a multiplicity of perforations, wherein said cover has various perforations over the length of the tampon so that a differentiated expansion of the tampon while absorbing fluid is achievable, wherein a degree of perforations of the cover increases towards the withdrawal end of the tampon at least over a portion of its length.

2. Tampon of claim 1, wherein the degree of perforation is increased by increasing the number of the perforations.

3. Tampon according to claim 1, wherein the perforations have an increased size in the direction of the withdrawal end of the tampon.

4. Tampon of claim 1, wherein at least some of the perforations have a conical configuration.

5. Tampon of claim 1, wherein perforations of different size are distributed over the length of the tampon.

6. Tampon of claim 5, wherein the perforations have an increased diameter in the direction of the withdrawal end of the tampon.

7. Tampon of claim 5, wherein the perforations have a greater dimension in the longitudinal direction of the tampon than in the circumferential direction of the tampon.

8. Tampon of claim 5, wherein an average distance between said perforations in the cover is reduced in the direction of the withdrawal end.

9. Tampon of claim 5, wherein the perforations begin directly next to the introduction end of the tampon and extend towards the withdrawal end of the tampon, wherein perforations proximate the introduction end and have relatively small dimensions changing and enlarged dimensions proximate the withdrawal end of the tampon.

10. Tampon of claim 5, wherein the degree of perforation decreases in the immediate proximity of the withdrawal end.

11. Tampon of claim 1, wherein the cover is an apertured plastic film.

12. Tampon, wherein the absorbent body is made from a section of a longitudinally extending fiber fleece web, a rear end of which is fastened to a front end of a strip of perforated cover material in the longitudinal direction of the fiber fleece web, of which, when the fiber fleece web section is rolled upon itself, the rear free end is securely connected to a front section of the cover strip as to form a tampon blank being substantially radially pressed to the main axis of the tampon blank, wherein the size of said perforation of the cover is at least partially increased in the direction of the withdrawal end of the tampon.

13. Tampon of claim 1, wherein said web comprises about 0.1 to about 0.4 gsm of a coating composition covering at least partially an outer surface of the web to form a coated portion.

14. Tampon according to claim 12, wherein said coating composition is applied at a coating weight of about 0.1 to about 0.4 gsm.

15. Tampon of claim 13, wherein said coating composition is applied at a coating weight of about 0.16 to about 0.36 gsm.

* * * * *